United States Patent [19]
Esmon et al.

[11] Patent Number: 5,847,085
[45] Date of Patent: Dec. 8, 1998

[54] MODIFIED PROTEIN C AND METHODS OF USE THEREOF

[75] Inventors: Charles T. Esmon; Mikhail D. Smirnov, both of Oklahoma City, Okla.

[73] Assignee: Oklahoma Medical Research Foundation, Oklahoma City, Okla.

[21] Appl. No.: 965,832

[22] Filed: Nov. 7, 1997

Related U.S. Application Data

[63] Continuation-in-part of Ser. No. 745,254, Nov. 8, 1996.

[60] Provisional application No. 60/053,768 Jul. 25, 1997.

[51] Int. Cl.$^6$ .................................................. A61K 35/14
[52] U.S. Cl. ......................... 530/381; 530/384; 530/350; 435/69.7; 435/69.1; 435/219; 435/471
[58] Field of Search ..................... 530/381, 384, 530/350; 435/69.7, 69.1, 219, 471

[56] References Cited

U.S. PATENT DOCUMENTS

| | | | |
|---|---|---|---|
| 4,968,626 | 11/1990 | Foster et al. | 435/320 |
| 5,225,537 | 7/1993 | Foster | 530/380 |

OTHER PUBLICATIONS

Geng et al. (1995) Biochem. 34, pp. 8449–8457.
Yu et al. (1994) Biochem. 33, pp. 823–831.
Zhong et al. (1993) Biotechniques 15/5, pp. 874–878.
Degan et al. (1987) Biochem. 26, pp. 6165–6177.
Geng et al. (Aug. 26, 1996) Thromb. Haemostasis, 76/2, pp. 205–207.

*Primary Examiner*—Robert A. Wax
*Assistant Examiner*—Enrique D. Longton
*Attorney, Agent, or Firm*—Arnall Golden & Gregory LLP

[57] ABSTRACT

Modified Protein C molecules have been made which substitute the gamma carboxylglutamic acid (Gla) region of another Vitamin K dependent protein, most preferably prothrombin, for the native region of the Protein C. A modified protein C molecules has been made which substitutes the gamma carboxyglutamic acid (Gla) region with the corresponding region of prothrombin. The modified or chimeric protein C has advantages over the wild-type protein C since it is less sensitive to inhibition by some natural antibody inhibitors of protein C (which would otherwise decrease the ability of the protein C to act as an anticoagulant) and which do not need the same cofactors or same amounts of cofactors, and can therefore be effective in patients with lowered levels of the cofactors such as protein S or the lipids present in elevated levels in platelets such as phosphatidyl ethanolamine (PE). The anticoagulant activity of the chimera was tested in normal and factor V Leiden plasma. The chimera was approximately ten times more effective in inhibiting factor V Leiden plasma clotting.

4 Claims, 3 Drawing Sheets

MODIFIED PROTEIN C AND METHODS OF USE THEREOF

BACKGROUND OF THE INVENTION

This application is a continuation in part of U.S. patent application Ser. No. 08/745,254 "Modified Protein C", filed Nov. 8, 1996, by Mikhail D. Smirnov and Charles T. Esmon, and U.S. provisional patent application Ser. No. 60/053,768 "Treatment of Factor V Leiden Patients with Modified Protein C" filed Jul. 25, 1997, by Charles T. Esmon.

The United States government has certain rights in this invention by virtue of grant No. P50 54502 awarded by the National Heart, Lung and Blood Institute of the National Institutes of Health to Naomi Esmon.

The present invention is generally in the area of the use of a modified protein C having enhanced anticoagulant activity to treat Factor V Leiden patients.

Protein C plays a major role in the regulation of blood coagulation. Patients deficient in protein C usually exhibit life threatening thrombotic complications in infancy (Seligsohn et al., (1984) *N. Engl. J. Med.* 310, 559–562; Esmon, (1992) *Trends Cardiovasc. Med.* 2, 214–220) that are corrected by protein C administration (Dreyfus et al., (1991) *N. Engl. J. Med.* 325, 1565–1568). In addition, activated protein C (APC) can prevent the lethal effects of *E. coli* in baboon models of gram negative sepsis (Taylor et al., (1987) *J. Clin. Invest.* 79; U.S. Pat. No. 5,009,889 to Taylor and Esmon) and preliminary clinical results suggest that protein C is effective in treating certain forms of human septic shock (Gerson et al., (1993) *Pediatrics* 91, 418–422). These results suggest that protein C may both control coagulation and influence inflammation. Indeed, inhibition of protein S, an important component of the protein C pathway, exacerbates the response of primates to sublethal levels of *E. coli* and augments the appearance of TNF in the circulation (Taylor et al., (1991) *Blood* 78, 357–363). The mechanisms involved in controlling the inflammatory response remain unknown.

Protein C is activated when thrombin, the terminal enzyme of the coagulation system, binds to an endothelial cell surface protein, thrombomodulin (Esmon, (1989) *J. Biol. Chem.* 264, 4743–4746; Dittman and Majerus, (1990) *Blood* 75, 329–336; Dittman, (1991) *Trends Cardiovasc. Med.* 1, 331–336). In cell culture, thrombomodulin transcription is blocked by exposure of endothelial cells to tumor necrosis factor (TNF) (Conway and Rosenberg, (1988) *Mol. Cell. Biol.* 8, 5588–5592) and thrombomodulin activity and antigen are subsequently internalized and degraded (Lentz et al., (1991) *Blood* 77, 543–550, Moore, K. L., et.al., (1989) *Blood* 73, 159–165). In addition, C4bBP, a regulatory protein of the complement system, binds protein S to form a complex that is functionally inactive in supporting APC anticoagulant activity in vitro (Dahlbäck, (1986) *J. Biol. Chem.* 261, 12022–12027) and in vivo (Taylor, et al., 1991). Furthermore, C4bBP behaves as an acute phase reactant (Dahlbäck, (1991) *Thromb. Haemostas.* 66, 49–61). Thus, proteins of this pathway not only appear to regulate inflammation, but they also interact with components that regulate inflammation, and they themselves are subject to down regulation by inflammatory mediators.

It is therefore an object of the present invention to provide a modified protein C which is useful as an improved anticoagulant.

It is a further object of the present invention to provide a method for treating patients with deficiencies in protein C and/or S and in the treatment of Factor V Leiden patients.

It is another object of the present invention to provide methods of modulating the inflammatory response involving protein C and activated protein C.

SUMMARY OF THE INVENTION

Modified Protein C molecules can be made which substitute the gamma carboxylglutamic acid (Gla) region of another Vitamin K dependent protein, most preferably prothrombin, for the native region of the Protein C. The modified or chimeric protein C has advantages over the wild-type protein C since it is less sensitive to inhibition by some natural antibody inhibitors of protein C (which would otherwise decrease the ability of the protein C to act as an anticoagulant) and does not need the same cofactors or same amounts of cofactors, and can therefore be effective in patients with lowered levels of the cofactors such as protein S or the lipids present in elevated levels in activated platelets such as phosphatidyl ethanolamine (PE).

As described in the examples, a chimeric protein C was designed after observing that supplementation of phosphatidylserine (PS) containing vesicles with PE enhances activated protein C (APC) anticoagulant activity. To determine the structural basis of the PE sensitivity, a chimeric molecule in which the Gla domain and hydrophobic stack (residues 1–45) of protein C were replaced with the corresponding region of prothrombin (PC-PT Gla) was constructed. The activated chimeric molecule is referred to as APC-PT Gla. APC inactivation of Factor Va was enhanced 10 fold by PE and 2 fold by protein S in either the presence or absence of PE. In purified systems, relative to the chimera, wild type APC inactivated factor Va more rapidly on PE containing vesicles and more slowly on vesicles lacking PE. With APC-PT Gla, inactivation of factor Va was only slightly enhanced by PE and was slightly inhibited by protein S. Prothrombin inhibited inactivation of factor Va by wild type APC much more effectively than the chimera, possibly accounting for the observation that the chimera exhibited approximately 5 fold more plasma anticoagulant activity than wild type APC under all conditions tested. These results demonstrate that the functional influence of PE on factor Va inactivation by APC is mediated by special properties unique to the Gla domain and that the Gla domain of protein C provides specialized functions to greatly enhance interaction with factor Va and protein S on PE containing membranes.

Additionally, the anticoagulant activity of the chimera was tested in normal and factor V Leiden plasma. The increase in clotting time as a function of increasing APC or chimera concentration was monitored. As the enclosed figures show, with the chimera, the clotting time rose almost linearly from 23 seconds with no APC, to 45 second with APC at one microgram/ml. In contrast, it took 10 micrograms/ml native APC to give a comparable anticoagulant response in the Leiden plasma. Unlike activated protein C, the anticoagulant activity was independent of protein S.

BRIEF DESCRIPTION OF THE DRAWINGS

FIG. 2A graphs the activity of APC and APC-PT Gla at concentrations of between 0 and 5.0 micrograms/ml; FIG. 2B is an expanded view of the activities at concentrations of between 0 and 1.0 micrograms/ml. Wild-type APC in combination with PE, no mAb (closed circles); wild-type APC in combination with PS and anti-protein S mAb (no protein S) (open triangles); wild-type APC in combination with PE and anti-protein S mAb (closed triangles); APC-PT Gla in combination with PE, no mAb (closed inverted triangle); APC-PT Gla in combination with PS, anti-protein S mAb (open diamonds); and APC-PT Gla in combination with PE, and anti-protein S mAb (closed diamonds).

DETAILED DESCRIPTION OF THE INVENTION

Assembly of multiprotein enzyme complexes on negatively charged phospholipid membrane surfaces is critical to both the formation and regulation of the blood clotting process. Zymogen activations occur rapidly when the enzyme, usually a vitamin K dependent protein, binds to a cofactor, usually a non-vitamin K dependent protein, to activate a substrate, usually a vitamin K dependent protein (reviewed in Mann, et al. (1988) Ann. Rev. Biochem. 57, 915–956; Furie and Furie (1988) Cell 53, 505–518). The enzymes and substrates interact with the membrane reversibly, while the cofactors may either bind reversibly or be integral membrane proteins. The nature of the phospholipid head group appears to contribute to catalytic and binding efficiency with phosphatidylserine (PS) being generally accepted as the most important phospholipid (Mann, et al. (1988); Pei, et al. (1993) J. Biol. Chem. 268, 3226–3233). The vast majority of biophysical and kinetic studies of the assembly of the vitamin K dependent complexes have used membranes composed solely of phosphatidylcholine (PC) and PS (Mann, et al., Pei, et al., Castellino, F. J. (1995) Trends Cardiovasc. Med. 55–62; Nelsestuen, (1978) Biochemistry 17, 2134–2138).

Recently, it was observed that phosphatidylethanolamine (PE), a major constituent of the outer leaflet of the membrane of activated platelets (Bevers, E. M., Comfurius, P., and Zwaal, R. F. A. (1983) Biochim. Biophys. Acta 736, 57–66), plays an important role in the function of one of these complexes, the activated protein C (APC) dependent inactivation of factor Va (Smirnov and Esmon (1994) J. Biol. Chem. 269, 816–819). In this case, the presence of PE or cardiolipin potently enhanced the rate of inactivation. Subsequently, roles for PE in factor VIII binding (Gilbert and Arena (1995) J. Biol. Chem. 270, 18500–18505), tissue factor-factor VIIa activation of factor X (Neuenschwander, et al. (1995) Biochemistry 34, 13988–13993) and prothrombin activation (Billy, et al. (1995) J. Biol. Chem. 270, 26883–26889; Smeets, et al. (1996) Thromb. Res. 81, 419–426) have been reported. In the case of prothrombin activation, with PE present, the amount of PS required to support prothrombin activation was reduced several fold. In the case of tissue factor, it was shown that the presence of PE enhanced activation primarily by decreasing the amount of PS required for optimal activation and this was largely a Km effect on the substrate. The impact of PE on the inactivation of factor Va was substantially greater than on the other systems. For prothrombin activation and tissue factor mediated factor X activation, the augmentation by PE could be overcome simply by increasing PS concentration whereas the PE impact on factor Va inactivation was not eliminated by high PS (Smirnov 1994).

Protein C, like the other vitamin K dependent proteins, is composed of several domains (Furie 1988). These include the protease domain, two EGF like domains, an aromatic stack and the vitamin K dependent Gla domain containing the 4-carboxyglutamic acid (Gla) residues. These Gla residues are involved in $Ca^{2+}$ dependent membrane binding and are clustered within the amino terminal 48 residues of the vitamin K dependent plasma factors (Furie 1988, Castellino 19954, Mann, K. G., Krishnaswamy, S., and Lawson, J. H. (1992) Sem. Hematol. 29, 213–226). The sequences of these proteins within this region are highly conserved, but the number of Gla residues varies from 9 to 12 (Furie 1988). Since the Gla domains are implicated in the membrane binding and membrane dependent catalytic activity, it was postulated that the differences in PE dependent behavior between protein C and the other complexes might be mediated by the Gla domains. To test this possibility, a chimeric form of protein C in which the Gla domain has been exchanged with that of prothrombin was designed in an effort to evaluate the regions of the molecules involved in the PE dependent activities.

The chimera was designed to be non-immunogenic in humans, as well as to have the advantageous properties demonstrated in the examples. Exons one to three of protein C were replaced with exons one to three of prothrombin. Exons one to three encode the pre-proleader of approximately 42 amino acids including a signal peptide required for proper "docking" of the protein with the carboxylase which carboxylates the Gla domain and which is cleaved from the mature protein, the Gla domain consisting of approximately 32 amino acids and the aromatic stack region, from residue 39 to 42 in human prothrombin. The splice sites in both protein C and prothrombin are identical, so that no sequence changes were required and only human sequence present in the naturally occurring human proteins is present in the chimeras. The activation site in the protein C zymogen was unaffected by the change.

The results of the studies reported below show that the substitution of the native Gla domain with the prothrombin Gla domain alters the activity of the protein C, decreasing the need for PE and protein S and reducing inhibition by prothrombin. The PE dependence of APC anticoagulant activity is clearly mediated in large part by the Gla domain of protein C. APC-PT Gla exhibited little dependence on the presence of PE in the liposomes in purified systems. Furthermore, the factor Va inactivating activity of the chimera was inhibited rather than stimulated by protein S. These differences were not due to defects in membrane binding since the chimera bound to membranes at least as well as wild type protein C and was more active than wild type vesicles devoid of PE while being slightly less active on vesicles containing PE. Much of this difference appears to lie in the capacity of protein S and factor Va to synergistically augment APC binding to vesicles, especially those containing PE. In particular, in the presence of factor Va, protein S failed to enhance binding of the chimera as it did in the case of wild type APC.

In plasma, the chimera exhibited much greater anticoagulant activity than wild type APC on vesicles with or without PE. These differences appeared to be due, in part, to the decreased ability of prothrombin to block factor Va inactivation by the chimera.

The PE effects on catalysis of the APC anticoagulant complexes have both a cell biology and pathophysiology ramification. PE has been reported to be present on the surface of unactivated cells (Wang, et al. (1986) *Biochem. Biophys. Acta* 856, 244–258) and, following activation, may constitute nearly 40% of the outerleaflet membrane phospholipid (Bevers, et al. 1983). Furthermore, PE has been reported to have a higher Km for the flipase and hence is likely to be more slowly transported to the inner membrane leaflet (Devaux (1991) *Biochemistry* 30, 1163–1173). Therefore, if the different coagulation complexes were to exhibit widely different PE:PS dependencies, this time dependent change in membrane composition could selectively favor clot promoting or clot inhibiting reactions.

Although demonstrated by the substitution of the Gla region of the protein C with the Gla region of prothrombin, many of the other Vitamin K dependent clotting factors are equally well understood and their Gla regions could be inserted in place of the N-terminal regions of protein C to create a chimera having altered anticoagulant activity. Moreover, although the chimera described in the examples was made by substituting exons one, two and three of prothrombin for those of protein C, one could actually only substitute a portion of the protein encoded by these exons. For example, one could substitute only the prothrombin Gla domain for the protein C domain, or only the Gla domain and the helical stack domains, since the pre-proleader from protein C would be expected to result in carboxylation of the Gla region. Unlike some systems, the coagulation system is highly predictable based on in vitro results and the highly conserved structure within the clotting proteins provides a means for extrapolation among proteins. Other representative donor proteins include factor X and factor VII. The chimeras are made using the same techniques described in detail in the example. The DNA sequences encoding the other Vitamin K dependent clotting factors are known and described in the literature.

Pharmaceutical Compositions

The protein is generally effective when administered parenterally in amounts above about 90 μg/kg of body weight, assuming 35 ml plasma/kg, approximately three to four micrograms protein C/ml plasma, and one to three micrograms chimeric protein C/ml plasma. Based on extrapolation from other proteins, for treatment of most inflammatory disorders, the dosage range will be between 20 and 200 micrograms/kg of body weight.

The modified protein C is preferably administered in a pharmaceutically acceptable vehicle. Suitable pharmaceutical vehicles are known to those skilled in the art. For parenteral administration, the compound will usually be dissolved or suspended in sterile water or saline. The activated form of the chimera may be a preferred agent in the treatment of particular disorders.

Disorders to be treated

It should be possible to treat disorders where protein S is low, some forms of lupus, following stroke or myocardial infarction, after venous thrombosis and in disseminated intravascular coagulation, septic shock, adult respiratory distress syndrome, and pulmonary emboli using the modified protein C. Protein S levels are often low in these conditions, making APC less effective as an anticoagulant (see D'angelo, et al. (1988) *J. Clin. Invest.* 81, 1445–1454). Examples of these conditions include disseminated intravascular coagulation, during warfarin anticoagulation, and in thromboembolic disease. Since the chimera's optimal activity does not depend on normal levels of protein S in the patient, it is expected to be an active anticoagulant in conditions where the patient's own activated protein C or therapeutically administered protein C or activated protein C would be compromised. Note that for technical reasons, protein S concentrates useful for treatment have not been successfully prepared.

Lupus anticoagulants and some antiphospholipid antibodies block the function of coagulation and anticoagulation complexes preferentially on PE containing membranes (Smirnov, et al. (1995) *J. Clin. Invest.* 95, 309–316; Rauch, et al. (1986) *J. Biol. Chem.* 261, 9672–9677). These antibodies are associated with an increased risk of thrombosis (Ginsberg, et al. (1993) *Blood* 81, 2958–2963; Triplett, D. A. (1993) *Arch. Pathol. Lab. Med.* 117, 78–88; Pierangeli, et al. (1994) *Thromb Haemostas.* 71, 670–674). In addition to therapeutic applications, the APC molecule with no PE dependence allows the exploration of the mechanisms of PE dependent lupus anticoagulant effects on the APC system in vitro and in vivo. The chimera is less sensitive to inhibition by lupus anticoagulants and hence can be used to identify pathogenic antibody populations that react with protein C.

It is also possible to treat patients with factor V Leiden using the protein C chimera. Factor V Leiden is a relatively common (approximately 5% of the population) polymorphism in Caucasians that results from a substitution of Gln for Arg at residue 506 in the factor Va molecule, described by Dahlbäck, "Inherited thrombophilia: resistance to activated protein C as a pathogenic factor of venous thromboembolism" *Blood* 85:607–614 (1995). This form of factor Va is resistant to inactivation by APC and is commonly referred to as Factor V Leiden because the site of the mutation was originally identified by the Leiden group, as reported by Bertina, et al., "Mutation in blood coagulation factor V associated with resistance to activated protein C" *Nature* 369:64–67 (1994). This Arg residue is one of the cleavage sites utilized by APC to inactivate factor Va, as described by Kalafatis, et al., "The mechanism of inactivation of human factor V and human factor Va by activated protein C" *J. Biol. Chem.* 269:31869–31880 (1994); Kalafatis, et al., "Characterization of the molecular defect in factor VR506Q. *J. Biol. Chem.* 270:4053–4057 (1995). Factor V Leiden is a risk factor for venous thrombosis and clinical studies have indicated that the polymorphism is found in about 20–60% of the patients with deep vein thrombosis, as reported by Florell, et al., "Inherited thrombotic disorders: An Update" *Am. J. Hematol.* 54:53–60 (1997). Since the polymorphism is so common, it would be an advantage to be able to inactivate factor V Leiden more rapidly to prevent thrombosis. This is especially true if protein C or APC were to be used in thrombotic therapy.

The effective dosage of protein C chimera or its activated form can be extrapolated from the clinical studies using protein C (wild-type) modified in view of the differences in activity shown by the examples.

The present invention will be more fully understood by reference to the following non-limiting examples. The following abbreviations are used herein: APC, activated protein C; PC-PT Gla, a chimeric molecule in which the Gla domain and hydrophobic stack (residues 1–45) of protein C has been replaced with the corresponding region of prothrombin; APC-PTGla, the activated form of PC-TTGla; PE, phosphatidylethanolamine; PS, phosphatidylserine; PC, phosphatidylcholine; Gla, 4-carboxyglutamic acid; X-CP, the factor X activator from Russell's viper venom; BSA, bovine serum albumin; TBS, 150 mM NaCl, 20 mM Tris-HCl, 0.02% sodium azide, pH 7.4; TBS-GOB, TBS containing 1 mg/ml gelatin, 1 mg/ml ovalbumin and 10 mg/ml BSA.

EXAMPLE 1

Construction of a chimeric Protein C-Prothrombin Protein.

EXPERIMENTAL PROCEDURES

Proteins and reagents. Human thrombin and prothrombin (Owen, et al. (1974) *J. Biol. Chem.* 249, 594–605), human APC (Esmon, et al. (1993) *Meths. Enzymol.* 222, 359–385), human protein S (Taylor, et al. (1991) *Blood* 78, 356–363), human factor Xa (Le Bonniec, et al. (1994) *J. Biol. Chem.* 267, 6970–6976), bovine factor Va (Esmon, C. T. (1979) *J. Biol. Chem.* 254, 964–973), and the factor X activator from Russell's viper venom (X-CP)(Esmon, C. T. (1973) (Ph.D. Dissertation), Washington University, St. Louis) were prepared as described. Meizothrombin labeled in the active site with fluorescein was prepared as described by Armstrong, et al. (1990) *J. Biol. Chem.* 265, 6210–6218; Bock (1988) *Biochemistry* 27, 6633–6639. Human factor Va was obtained from Hematologic Technologies. Bovine serum albumin (BSA), Russell's viper venom, ovalbumin, gelatin, MOPS, Tris-HCl and salts were obtained from Sigma. The chromogenic substrates Spectrozyme TH and Spectrozyme PCa were obtained from American Diagnostica (Greenwich, Conn.). The irreversible inhibitor of the serine proteases (p-amidinophenyl)-methanesulphonyl fluoride was obtained from Calbiochem. 1-palmitoyl-2-oleoyl-sn-glycero-3 PS, 1-palmitoyl-2-oleoyl-sn-glycero-3 PC and 1,2-dilinoleoyl-sn-glycero-3-PE were obtained from Avanti Polar Lipids Inc. 1-Palmitoyl-2-[1-$^{14}$C-oleoyl]PC was obtained from DuPont NEN. Factor V deficient human plasma was obtained from George King Bio-Medical, Inc. (Overland Park).

Preparation of phospholipid vesicles.

Sonicated vesicles were prepared as described (Smirnov 1994). Briefly, lipids were mixed in the weight proportions described below, dried under argon and lyopholized overnight to remove organic solvents. They were then reconstituted in 150 mM NaCl, 20 mM Tris-HCl, 0.02%, sodium azide, pH 7.4 (TBS) to 2 mg total lipid/ml and sonicated (Bronson Sonic Power Co, model 350) 15 min in an ice-water bath under argon flow, centrifuged at 8000 g for 15 min and filtered through a 0.22 $\mu$m filter. The vesicles were used immediately or stored at +20° C. Storage did not alter vesicle activity.

Construction of the protein C prothrombin Gla domain chimera.

The protein C chimera was constructed in which the first 3 exons of prothrombin (i.e. coding for the pre-proleader, the Gla domain and the aromatic stack regions) replaced the corresponding regions of protein C.

The relevant amino acid sequences for human prothrombin and protein C are:

human prothrombin (Sequence ID No. 1): ANTFLxxVRKGNLxRxCVxxTCSYxxAFxALxSSTATDVFWAKYT human protein C (Sequence ID No. 2): ANSFLxxLRHSSLxRxCIxxICDFxxAKxIFQNVDDTLAFWSKHV where x means gamma carboxylglutamic acid.

Mutagenesis was performed by polymerase chain reaction methodology. The wild type protein C cDNA (provided by Eli Lilly Research Laboratory) was ligated into the HindIII and XbaI sites of pRc/RSV (Invitrogen, CA) to form RSV-PC as described by Rezaie 1993. There is a unique BstEII restriction site in the protein C CDNA in the beginning of exon 4, which encodes the N-terminal EGF domain. Double digestion of RSV-PC with HindIII and BstEII removes the DNA sequences of the first 3 exons of protein C as well as the first codon of exon 4, which is an Asp. To exchange exons one to three of protein C with those of prothrombin, two PCR primers were synthesized. The forward prothrombin sense primer 5'-CGCT<u>AAGCTT</u>CCATGGCCCGCATCCGAGGCTT-3' (Sequence ID No. 3) starts from the initiation codon of the prothrombin cDNA (provided by Dr. Ross MacGillivray) and contains a HindIII restriction enzyme site at the 5'-end of the primer (underlined). The reverse prothrombin antisense primer 5'-GAGTGGTCACCGTCTGTGTACTTGGCCC-AGAACA-3' (Sequence ID No. 4) starts from the nucleotide of exon 3 in the prothrombin cDNA and contains the native BstEII restriction enzyme site containing the missing Asp codon in the beginning of exon 4 of the protein C cDNA.

Following PCR amplification of prothrombin cDNA with these two primers and double digestion with HindIII and BstEII, the DNA fragment was ligated into the identical sites of the wild type protein C expression vector described above.

After sequencing, the mutant construction was transfected into human 293 cells and the chimeric protein C was purified from culture supernatants by immunoaffinity chromatography using the calcium dependent monoclonal antibody, HPC4, as described by Rezaie and Esmon (1993) *J. Biol. Chem.* 268, 19943–19948, Rezaie, A. R. and Esmon, C. T. (1992) *J. Biol. Chem.* 267, 26104–26109). The PC-PT Gla chimera was activated to form APC-PT Gla by thrombin in the presence of 2 mM EDTA and purified by Mono-Q FPLC chromatography (Pharmacia) essentially as described for wild type protein C by Esmon, C. T., et al., *Methods. Enzymol.* 222, 259–385 (1993).

Gla residue determinations were performed by Dr. Betty Yan and Cindy Payne at Eli Lilly Research Laboratory. The Gla content per mole protein obtained were: 8.7±0.3 for protein C, 10.9±0.2 for prothombin, 9.5±0.2 for PC-PT Gla and 10.3±0.4 for APC-PT Gla.

EXAMPLE 2

Determination of protein C chimeric protein activity.

Methods and materials

Measurement of APC factor Va inactivation and prothrombinase activity in the purified system.

Factor Va inactivation was analyzed with a three stage assay essentially as described by Smirnov and Esmon (1994). Briefly, factor Va was inactivated by APC or APC-PTGla in the first stage. In the second stage, after inactivation of the enzyme with (p-amidinophenyl)-methanesulphonyl fluoride, residual factor Va activity was monitored by its activity in the prothrombinase complex in the presence of excess factor Xa and prothrombin. The resultant thrombin was measured in the third stage using a chromogenic assay. All reagents were diluted in TBS containing 1 mg/ml gelatin, 1 mg/ml and 10 mg/ml BSA (TBS-GOB). Percent factor Va inactivation was calculated by dividing thrombin formation in the presence of APC by thrombin formation in its absence and subtracting this value from 1.

Enzyme was added at concentration of 0.002, 0.005, 0.01, 0.02, 0.05, 0.1, 0.15, 1 and 4 ng/ml. When held constant, the final concentration of reagents were 0.2 nM factor Va, 1 nM factor Xa, 1.4 $\mu$M prothrombin and 10 $\mu$g/ml phospholipid.

Clotting Assays.

Clotting assays were performed by a modification of the dilute Russell's viper venom test. Purified X-CP was employed instead of crude venom. All reagents were diluted in TBS containing 1 mg/ml gelatin. Assays were performed in 96-well plates. To serial dilutions of APC (30 $\mu$l) were added 10 $\mu$l of 60 $\mu$g/ml phospholipid, 10 $\mu$l of 20 ng/ml X-CP and 10 $\mu$l of normal pooled plasma. The entire mixture was incubated for 1 min. Clotting was initiated by addition of 25 $\mu$l of 20 mM $CaCl_2$. The clotting time was determined on a Vmax Kinetic Microplate Reader.

Adsorption of liposomes onto latex.

A 10% suspension of latex beads (50 $\mu$l) was pelleted in Eppendorf tubes and washed 3 times with PBS by centrifugation at 8,000×g for 1 min and resuspended in 50 $\mu$l TBS, 5 mM $CaCl_2$. Liposomes (100 $\mu$l at 1 mg/ml total phospholipid in TBS) were added and incubated 2 hr at 370° C. with shaking. After two washes, the beads were resuspended in TBS-GOB and further incubated 2 hr at room temperature with shaking. After 2 additional washes with TBS, the beads were resuspended in 500 $\mu$l TBS. Total phospholipid concentration was determined by counting the $^{14}$C-PC tracer included in the phospholipid mixtures (Beckman Model LS 6000SE scintillation counter) and found to be 50 $\mu$g/ml of latex suspension for both PS:PC and PE:PS:PC adsorbed liposomes. The beads could be stored at 4° C. for at least 7 days without loss of adsorbed phospholipid.

Fluorescent labelling.

Active site fluorescein labeled enzymes were prepared according to the method of Bock (1988). Briefly, to 300 $\mu$l of enzyme (1 mg/ml) were added 40 $\mu$l 1M HEPES, pH 7.4, 1 $\mu$l 0.2M EDTA and two times 5 $\mu$l of $N^\alpha$-[(acetylthio)acetyl]-D-Phe-Pro-Arg-$CH_2$Cl (4 mM), 10 min per incubation, to form ATA-FPR-enzyme. After overnight dialysis, 45 $\mu$l hydroxylamine (1M in 1M HEPES, pH 7.4) and 50 $\mu$l of 5-(iodoacetamido)-fluorescein (Molecular probes, 1 mg/ml in 1M HEPES, pH 7.4) were added to the ATA-FPR-enzymes and incubated 1 h at 0° C. Free fluorescein was removed by gel filtration on a PD-10 column (Pharmacia), and the samples were then dialyzed overnight at 4° C. With this method, each molecule of labelled enzyme contains a single dye at the same location and thus, all of the fluorescent molecules behave equivalently.

Binding of fluorescein labelled proteins to liposomes adsorbed on latex.

Liposome adsorbed latex beads (0.5 $\mu$g total phospholipid/ml) were suspended in TBS-GOB containing 2.5 mM $CaCl_2$. Appropriate protein(s) were added at the concentrations indicated and incubated at 25° C. for 20 min in the dark with occasional mixing. Binding was analyzed on a FACScan flow cytometer (Becton Dickinson). To determine the calcium independent, irreversible component of the fluorescent APC binding, 50 mM EDTA was added in 200 mM MOPS, pH 7.4 to a final concentration of 10 mM, and samples were re-analyzed after 20 min incubation in the dark. This component accounted for less than 20% of the observed binding.

Binding parameters were determined by fitting the calcium dependent binding to the equation for single site binding model using the ENZFITTER™ program (Elsevier Biosoft, Cambridge, UK).

Liposome-protein interactions measured by right angle light scattering.

Right angle light scattering was performed as described by Nelsestuen (1978) and Castellino (Zhang and Castellino 1993) on an SLM 8000 fluorimeter (SLM Instruments, Urbana, Ill.) with the wavelength set at 320 nm. The liposome concentration was 50 $\mu$g/ml. Binding experiments were performed in TBS, pH 7.4 containing 5 mM $CaCl_2$. The prothrombin and protein C concentrations were varied from 0 to 3 $\mu$M, and the PC-PT Gla concentrations were varied from 0 to 1.2 $\mu$M. Binding parameters were determined by fitting the reversible calcium dependent binding to the equation for single-site binding model using the ENZFITTER program.

Results

PC-PT Gla could be activated to form an enzyme with amidolytic activity toward Spectrozyme PCa equivalent to wild type APC. The concentration dependence of inactivation of factor Va between APC and the APC chimera on vesicles with or without PE supplementation was then compared. On vesicles composed solely of PS:PC, the chimera was approximately 5 times more active than wild type APC. PE enhanced factor Va inactivation by the chimera very little (about 1.6 fold in this experiment) compared to approximately a 15 fold enhancement of APC. In addition, protein S (2.5 $\mu$g/ml protein S) inhibited factor Va inactivation by the chimera whereas protein S enhanced factor Va inactivation by APC. These effects were not PE dependent. Therefore, it appears that much of the PE dependence of APC is mediated by the Gla domain and that some portion of the Gla domain is important for protein S mediated effects in purified systems.

To ascertain whether the differences in activity were reflected in differences in binding affinity to membranes, light scattering experiments were initially performed with prothrombin, protein C and PC-PT Gla on PS:PC vesicles containing either 20 or 50% PS. Prothrombin, protein C and PC-PT Gla were bound to liposomes (20%PS:80%PC liposomes) (50 $\mu$g/ml) in TBS, pH 7.4 containing 5 mM $CaCl_2$. Protein binding was measured by right angle light scattering.

It was apparent that the amount of prothrombin bound to the vesicles containing 20% PS was much higher than the amount of protein C bound with the PC-PT Gla being somewhat greater than the protein C. The Kd values were similar for all proteins. Increasing the PS concentration to 50% increased the amount of protein C and chimera binding more than two fold, but had a relatively small effect on prothrombin binding. From these experiments it is apparent that the PC-PT Gla binds to membranes at least as well protein C, but the affinity is not significantly better than wild type and hence cannot account for the increased activity on PS vesicles. The differences in maximum binding between the protein C and prothrombin presumably reflects the maximum number of molecules bound per liposome and the approximately 20% larger molecular mass of prothrombin.

It was possible that the differences in activity between wild type and the chimera reflect differences in interaction with other protein components, and therefore light scattering approaches could not be employed easily. Furthermore, PE containing vesicles are too large to utilize in light scattering approaches. Therefore, different binding methodologies had to be employed that would allow the presence of PE and/or other protein components. This was accomplished by flow cytometry. Liposomes adsorbed to latex were employed and binding was monitored as a function of increasing fluorescent enzyme concentration. The final concentration of phospholipid was 0.5 µg/ml, and, when present, protein S (pro S) was 100 nM and factor Va (FVa) was 10 nM. All flow cytometric measurements were done with the enzymes labeled in the active site with fluorescein. All light scattering experiments were performed with the zymogens except the meizothrombin experiments in which the enzyme activity was blocked with D-Phe-Pro-Arg chloromethylketone as described by Armstrong, et al. (1990). On PS:PC vesicles, the concentration dependence of binding of protein C by light scattering and the concentration dependence of APC binding to latex adsorbed vesicles was indistinguishable, thereby validating this approach. The data from the light scattering measurements and the flow cytometric analysis was plotted as a function of increasing protein concentration. The curves were overlayed after normalizing the curves to the maximum binding calculated with the Enzfitter program assuming a single class of binding sites. The Kd values for prothrombin and meizothrombin were also similar as determined by light scattering, and the meizothrombin binding was equivalent by the two methods, further validating this approach.

The major feature distinguishing wild type and APC-PT Gla is the degree to which protein S and factor Va synergize to augment membrane binding. Comparison of the chimera and wild type APC reveals that the binding affinity of wild type APC is higher than that of the chimera on PE containing vesicles when both factor Va and protein S are present and weaker when binding is examined on phospholipid devoid of PE. Factor Va alone and protein S alone had relatively little influence on the binding affinity of wild type APC, but factor Va alone enhanced chimera binding to a greater extent than wild type, especially in the absence of PE.

Their ability to anticoagulate plasma was then studied to determine whether these differences in properties between APC and the chimera were retained under more physiological conditions. Surprisingly, the chimera exhibited much higher anticoagulant activity than APC on vesicles with or without PE. Unlike the situation with purified proteins, in plasma the chimera was much more active than wild type APC on PE containing vesicles.

The much greater anticoagulant activity of the chimera in plasma could be due either to producing interactions specific to the chimera or, more likely, resistance to inhibitory factors. One possible inhibitor is prothrombin which circulates at very high concentrations. In principal, prothrombin could interfere with APC more effectively than with the chimera. To test this possibility, and the potential effect of protein S on this interaction, factor Va inactivation was analyzed as follows: Inactivation of factor Va by APC occurring in 30 minutes in the presence of 2.5 µg/ml protein S on PS:PC vesicles was defined as the standard condition. The concentration of APC required to inactivate 50% of the factor Va under the standard conditions was assigned a relative activity of 1. The concentration of APC or chimera required to inhibit 50% of the factor Va under various experimental conditions (±prothrombin, ±protein S, ±PE in the vesicles) in the first stage of the assay was then determined. This value was divided into the APC concentration determined for the standard condition to determine the relative activity.

Factor Va inactivation was performed as usual with the exception that 1.4 µM prothrombin was present in the first stage of the assays. Three concentrations of protein S: 0 µg/ml, 2.5 µg/ml, and 5 µg/ml were employed. Lipids were either PS:PC or PE:PS:PC. The relative activity was calculated as described above. Comparison of factor Va inactivation in the absence and the presence of prothrombin indicated that prothrombin inhibited APC inactivation of factor Va on either type of vesicle and independent of the presence of protein S. Prothrombin inhibited factor Va inactivation 5 fold in the absence of PE and nearly 100 fold in the presence of PE. In contrast, the chimera was much less sensitive to prothrombin, with inhibition of about 5 fold observed in the presence or absence of PE. This decreased sensitivity to prothrombin inhibition may account in part for the enhanced plasma anticoagulant activity of the chimera.

EXAMPLE 3

Use of chimeric protein as a research reagent.

In plasma, protein S plays additional roles in the anticoagulant activity of APC. For instance, previous studies have shown that protein S can block the ability factor Xa to protect factor Va (Solymoss, et al. (1988) *J. Biol. Chem.* 263, 14884–14890) from inactivation and that protein S can interfere directly with the assembly of the prothrombinase complex (Heeb, et al. (1993) *J. Biol. Chem.* 268, 2872–2877).

To test the possibility that one or more of these influences of protein S were observed with the chimera on PE containing vesicles, protein S was blocked with an inhibitory monoclonal antibody and the anticoagulant activities of activated protein C and the chimera were examined in plasma. Plasma clotting was performed under standard conditions in the presence and absence of an inhibitory monoclonal antibody to protein S (300 µg/ml of the protein S inhibitory monoclonal antibody S155 present in the final clotting mixture).

In plasma, the anticoagulant activity of the chimera remained relatively insensitive to protein S (i.e., the anticoagulant activity was not affected by antibody on vesicles devoid of PE (20%PS:80%PC liposomes) and only slightly reduced on vesicles containing PE (50%PE:20%PS:30%PC liposomes)). Unlike activated protein C, the anticoagulant activity was independent of protein S. Thus, protein S functions in plasma appear to be largely dependent on specific properties contributed by the protein C Gla domain.

EXAMPLE 4

Inactivation of factor Va Leiden using Protein C chimera.

Figure 1:
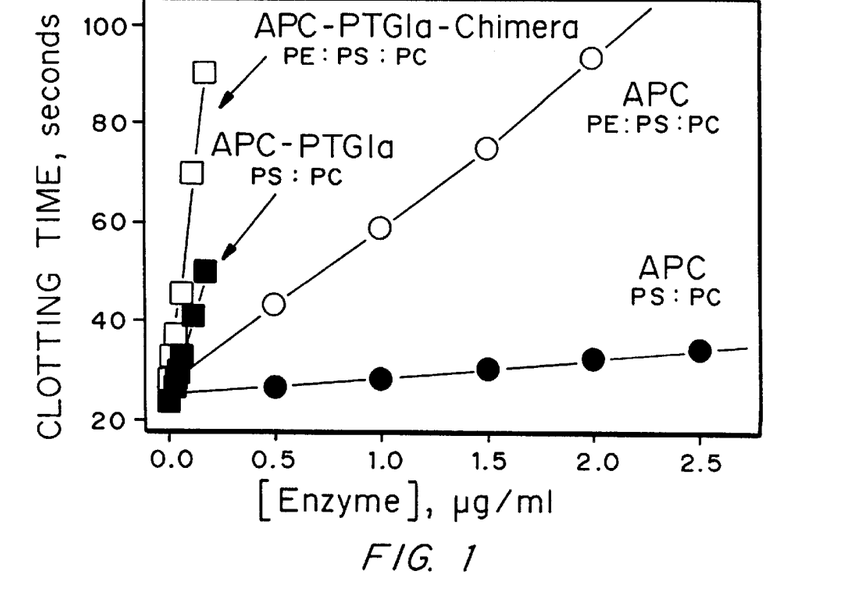
FIG. 1 is a graph showing the anticoagulant activities of APC and APC-PTGla. Clotting time (seconds) is plotted against enzyme concentration (micrograms/ml) for APC-PT Gla in the presence of PE:PS:PC (open squares); APC-PT Gla in the presence of PS:PC (closed blocks); APC in the presence of PE:PS:PC (open circles); and APC in the presence of PS:PC (closed circles).
Figure 2A:
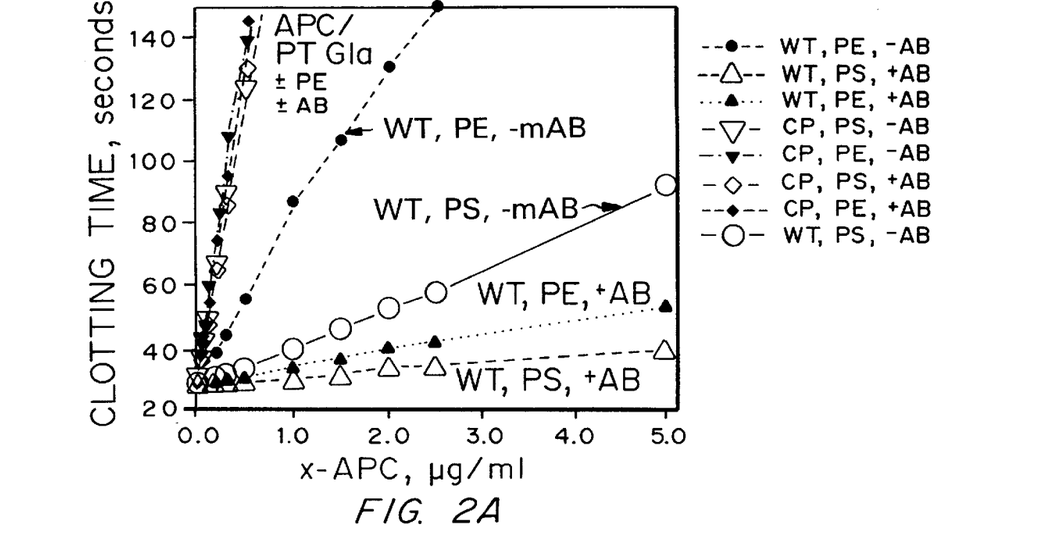
FIGS. 2A and 2B are graphs showing the influence of an antibody to protein S, anti-protein S MAB S155, on the activity of wild-type APC and APC-PT Gla in normal plasma, plotting clotting time (seconds) against concentration of APC or APC-PT Gla (micrograms/ml).
Figure 2B:
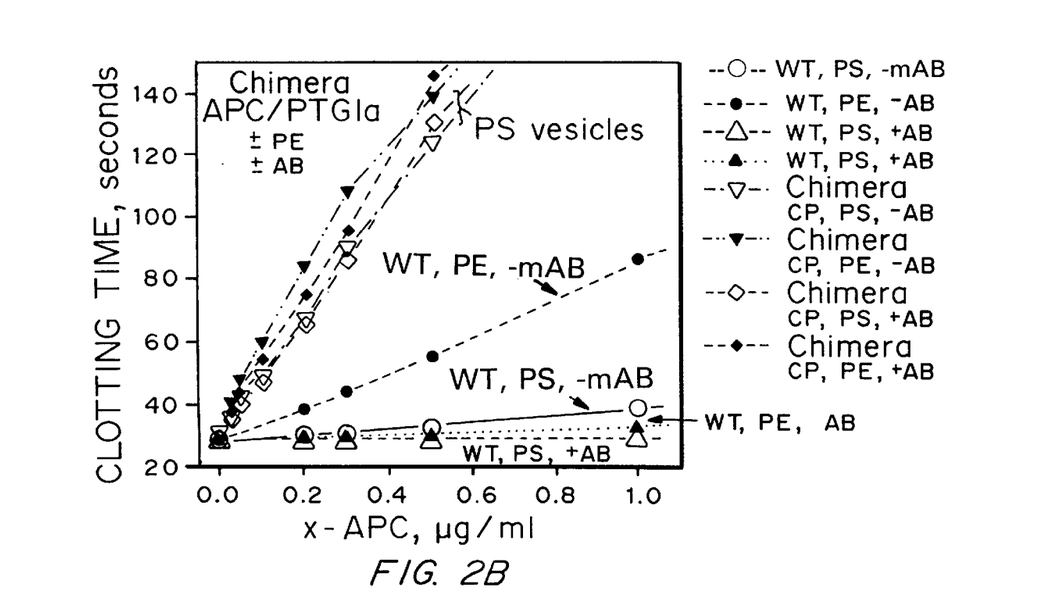
Figure 3A:
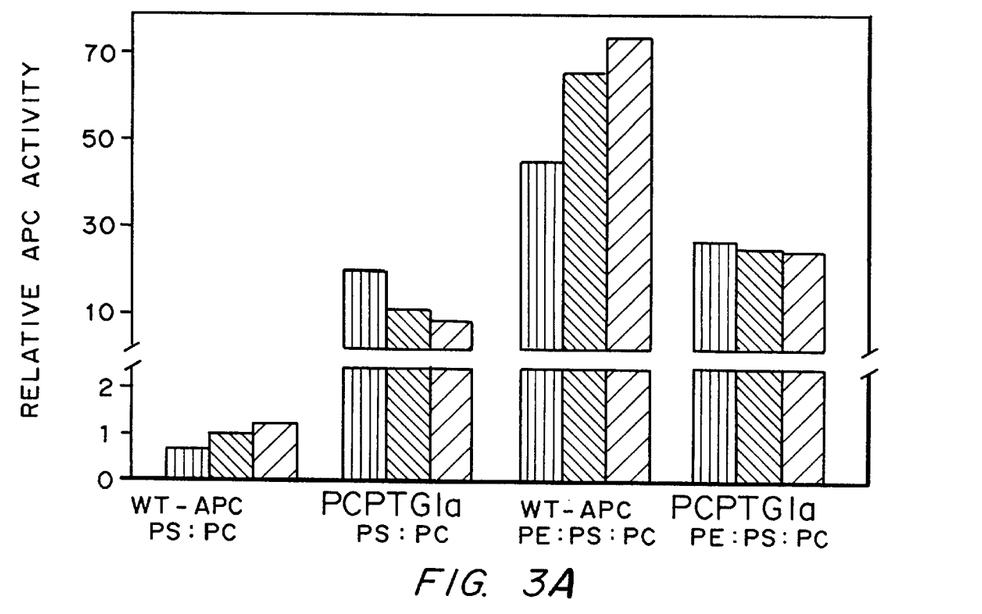
FIGS. 3A and 3B are graphs comparing the relative activity of wild-type APC in combination with PS:PC, PC-PT Gla in combination with PS:PC, wild-type APC in combination with PE:PS:PC, and PC-PT Gla in combination with PE:PS:PC, in the presence (FIG. 3B) and absence (FIG. 3A) of prothrombin at a physiological concentration of 1.4 micromolar. The APC concentration required in the presence of protein S and vesicles without PE is defined as one. Relative activity is calculated as the concentration under standard conditions required to inhibit 50% activity in 30 minutes divided by the concentration under experimental conditions required to inhibit 50% activity in 30 minutes.
Figure 3B:
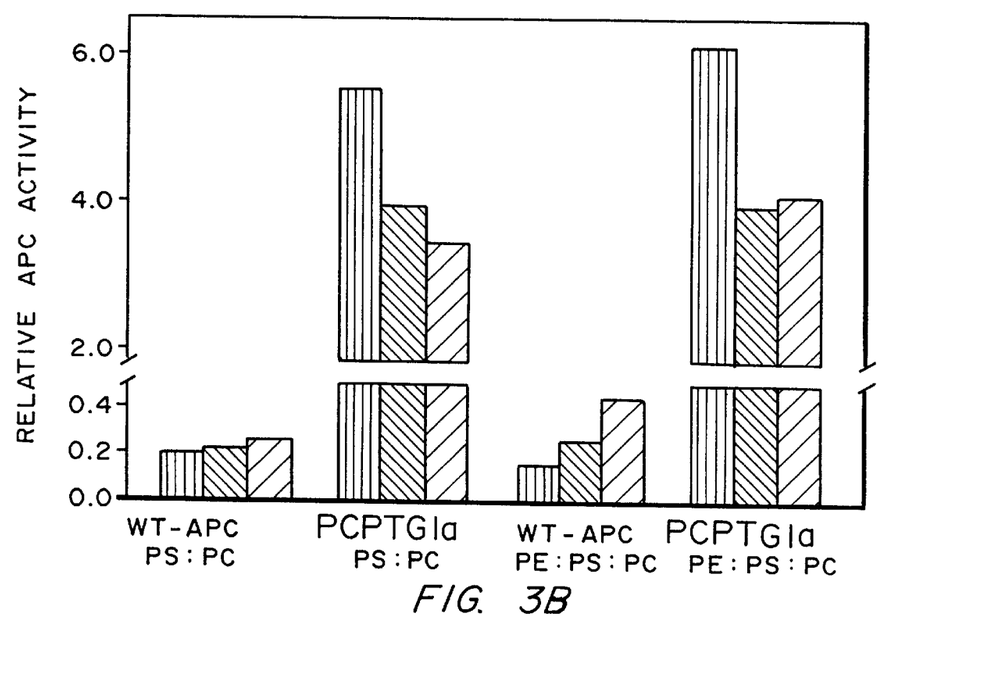
Figure 4:
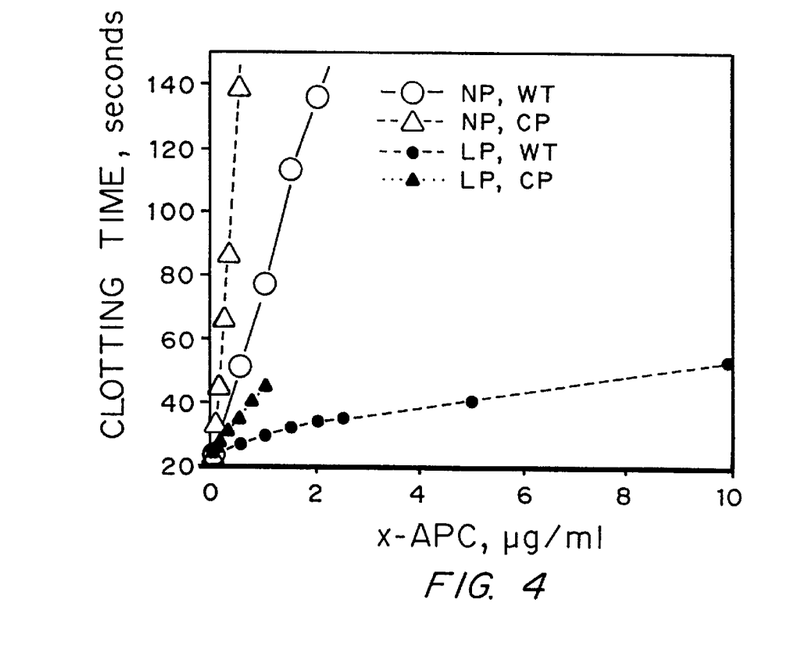
FIG. 4 is a graph of clotting times showing the activity of wild-type APC and APC/PTGla in normal and factor V-Leiden plasma, comparing the activity at concentrations of APC up to ten micrograms/ml.

The anticoagulant activity of the chimera was tested in normal and factor V Leiden plasma. Plasma clotting was determined with the following amounts of reagents: 20 microliters of APC or chimera to give the final concentrations in the assay shown in the figure, 10 microliters of 0.1 mg/ml phospholipid (50% phosphatidylethanolamine: 20% phosphatidylserine: 30% phosphatidylcholine), 10 microliters of 0.05 micrograms/ml of the factor X activating enzyme from Russell's viper venom, 20 microliters of normal plasma or Leiden plasma, and clotting was initiated by the addition of 20 microliters of 20 mM $CaCl_2$. The reactions were carried out at room temperature and clotting was monitored in a Vmax kinetic plate reader.

The results are shown in FIG. 4. As the figure shows, with the chimera, the clotting time of Leiden plasma rose almost linearly from 23 seconds with no APC to 45 seconds with the chimera at one microgram/ml (solid triangles). In contrast, it took 10 micrograms/ml native APC to give a comparable anticoagulant response in the Leiden plasma (solid circles). For comparison, the response of normal plasma to APC (open circles) or the chimeras are also shown. As shown previously, the chimera is more active than APC in normal plasma.

The teachings of the references cited herein are specifically incorporated herein.

Modifications and variations of the present invention will be obvious to those skilled in the art from the foregoing detailed description and are intended to be encompassed by the following claims.

We claim:

1. An isolated mammalian protein C chimeric protein wherein the gamma carboxylglutamic acid region of the protein C has been replaced with the gamma carboxyl-glutamic acid region of prothrombin.

2. The protein of claim 1 further comprising the helical stack region of prothrombin.

3. The protein of claim 2 wherein amino acids one to 45 of protein C are replaced by amino acids one to 45 of prothrombin.

4. The protein of claim 1 wherein the protein C and the prothrombin are human proteins.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY:
( B ) LOCATION: 6, 7, 14, 16, 19, 20, 25, 26, 29, 32
( D ) OTHER INFORMATION: /note= "where Xaa means gamma carboxylglutamic acid"

( i x ) FEATURE:
( A ) NAME/KEY:
( B ) LOCATION:
( D ) OTHER INFORMATION: /note= "partial sequence of human prothrombin"

( x i ) SEQUENCE DESCRIPTION: SEQ ID NO:1:

```
Ala Asn Thr Phe Leu Xaa Xaa Val Arg Lys Gly Asn Leu Xaa Arg Xaa
1               5                   10                  15

Cys Val Xaa Xaa Thr Cys Ser Tyr Xaa Xaa Ala Phe Xaa Ala Leu Xaa
            20                  25                  30

Ser Ser Thr Ala Thr Asp Val Phe Trp Ala Lys Tyr Thr
        35                  40                  45
```

( 2 ) INFORMATION FOR SEQ ID NO:2:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY:
( B ) LOCATION: 6, 7, 14, 16, 19, 20, 25, 26, 29
( D ) OTHER INFORMATION: /note= "where Xaa means gamma carboxylglutamic acid"

( i x ) FEATURE:
( A ) NAME/KEY:
( B ) LOCATION:
( D ) OTHER INFORMATION: /note= "partial sequence of human protein C"

( x i ) SEQUENCE DESCRIPTION: SEQ ID NO:2:

```
Ala Asn Ser Phe Leu Xaa Xaa Leu Arg His Ser Ser Leu Xaa Arg Xaa
```

```
         1               5                    10                    15
Cys  Ile  Xaa  Xaa  Ile  Cys  Asp  Phe  Xaa  Xaa  Ala  Lys  Xaa  Ile  Phe  Gln
               20                      25                    30

Asn  Val  Asp  Asp  Thr  Leu  Ala  Phe  Trp  Ser  Lys  His  Val
          35                      40                      45
```

(2) INFORMATION FOR SEQ ID NO:3:

(i) SEQUENCE CHARACTERISTICS:
        (A) LENGTH: 32 nucleic acids
        (B) TYPE: nucleic acid
        (C) STRANDEDNESS: single
        (D) TOPOLOGY: linear     (ii) MOLECULE TYPE: synthetic DNA     (ix) FEATURE:
        (A) NAME/KEY:
        (B) LOCATION:
        (D) OTHER INFORMATION: /note= "forward prothrombin sense primer with restriction site adapter"

(xi) SEQUENCE DESCRIPTION: SEQ ID NO:3:

```
CGCTAAGCTT   CCATGGCCCG   CATCCGAGGC   TT                                    32
```

(2) INFORMATION FOR SEQ ID NO:4:

(i) SEQUENCE CHARACTERISTICS:
        (A) LENGTH: 34 nucleic acids
        (B) TYPE: nucleic acid
        (C) STRANDEDNESS: single
        (D) TOPOLOGY: linear     (ii) MOLECULE TYPE: synthetic DNA     (ix) FEATURE:
        (A) NAME/KEY:
        (B) LOCATION:
        (D) OTHER INFORMATION: /note= "reverse prothrombin antisense primer"

(xi) SEQUENCE DESCRIPTION: SEQ ID NO:4:

```
GAGTGGTCAC   CGTCTGTGTA   CTTGGCCCAG   AACA                                  34
```